(12) United States Patent
Jenkins et al.

(10) Patent No.: US 7,790,766 B2
(45) Date of Patent: Sep. 7, 2010

(54) PHARMACEUTICAL COMPOSITIONS OF SHORT-ACTING SEDATIVE HYPNOTIC AGENT

(75) Inventors: Thomas E. Jenkins, La Honda, CA (US); Jennifer Bolton, San Francisco, CA (US)

(73) Assignee: Theravance, Inc., So. San Francisco, CA (US)

( * ) Notice: Subject to any disclaimer, the term of this patent is extended or adjusted under 35 U.S.C. 154(b) by 1430 days.

(21) Appl. No.: 10/895,603

(22) Filed: Jul. 21, 2004

(65) Prior Publication Data

US 2005/0020674 A1     Jan. 27, 2005

Related U.S. Application Data

(60) Provisional application No. 60/489,559, filed on Jul. 23, 2003.

(51) Int. Cl.
*A61K 31/265* (2006.01)
*A61K 31/4172* (2006.01)
*A61K 9/107* (2006.01)

(52) U.S. Cl. ............... 514/488; 514/560; 514/538; 514/816; 514/937

(58) Field of Classification Search ............ 514/488, 514/560, 538, 815, 937
See application file for complete search history.

(56) References Cited

U.S. PATENT DOCUMENTS

| | | | |
|---|---|---|---|
| 3,086,978 A | 4/1963 | Hiltman et al. | |
| 3,484,527 A | 12/1969 | Arnold et al. | |
| 3,510,559 A | 5/1970 | Arnold et al. | |
| 3,511,877 A | 5/1970 | Arnold et al. | |
| 4,401,830 A | 8/1983 | Umumura et al. | |
| 4,415,556 A * | 11/1983 | Bretschneider | 424/677 |
| 4,711,902 A | 12/1987 | Serno | |
| 4,798,846 A | 1/1989 | Glen et al. | |
| 4,918,092 A | 4/1990 | Frenette et al. | |
| 5,092,838 A | 3/1992 | Faict et al. | |
| 5,242,944 A | 9/1993 | Park et al. | |
| 5,714,520 A | 2/1998 | Jones et al. | |
| 6,028,108 A | 2/2000 | George | |
| 6,140,373 A | 10/2000 | May et al. | |
| 6,140,374 A | 10/2000 | May et al. | |
| 6,147,122 A | 11/2000 | Mirejovsky et al. | |
| 6,177,477 B1 | 1/2001 | George et al. | |
| 6,281,175 B1 | 8/2001 | Lyons et al. | |
| 6,469,069 B1 | 10/2002 | Mirejovsky et al. | |
| 6,726,919 B2 | 4/2004 | Pace et al. | |
| 6,887,866 B2 * | 5/2005 | Jenkins et al. | 514/217.11 |
| 7,015,346 B2 | 3/2006 | Jenkins et al. | |
| 7,514,425 B2 | 4/2009 | Jenkins et al. | |
| 2003/0134908 A1 | 7/2003 | Jones et al. | |
| 2003/0153554 A1 | 8/2003 | Jenkins et al. | |

FOREIGN PATENT DOCUMENTS

| | | |
|---|---|---|
| DE | 1134981 | 8/1962 |
| DE | 1518819 | 12/1969 |
| DE | 2731460 | 1/1978 |
| EP | 0 236 280 A1 | 9/1987 |
| GB | 906250 | 5/1961 |
| GB | 941694 | 11/1963 |
| GB | 1032872 | 6/1966 |
| GB | 1571395 | 7/1980 |
| GB | 961265 | 10/2008 |
| JP | 60-38343 | 2/1985 |
| WO | 9632135 | 10/1996 |
| WO | WO 2004/037750 A2 | 5/2004 |

OTHER PUBLICATIONS

Jenkins et al. Abstracts from the Society of Intravenous Anaesthesia (UK)'s Annual Scientific Meeting in Glasgow, May 30-31, 2003, Anaesthesia, 2004 59 pp. 100-102.*
Klockgether-Radke et al., Anesthesia with propanidid in a liposomal preparation. An experimental study in swine, Anaesthesist, Aug. 1995; 44(8) abstract in English.*
Anesthesiology, Longnecker et al., 2007, McGraw-Hill Professional, pp. 865-866.*
Anaesthesia News, No. 194 Sep. 2003, pp. 1-24.*
Bobey et al., "Selection of Disodium Edetate as the Optimal Antimicrobial Additive for Use in Propofol Emulsion", Antimicrobial Additive, vol. 25, No. 11, pp. 589-603 (2000).
Physicians' Desk Reference, PDR 56 Edition 2002, p. 687 and pp. 863-864 (2002).
Stevens et al., "Lipid Emulsions as Drug Delivery Systems", Business Briefing:Pharmatech 2003, pp. 1-4 (2003).
"SUBLIMAZE® 2ml injection, 10ml injection" 4 pages. South African Electronic Package inserts. Published by Malahyde Information Systems. Publication date Apr. 19, 1984, Jan. 21, 1983.
Wabel, Christoph, "Dissertation von Christoph Wabel: Influence of Lecithin on Structure and Stability of Parenteral Fat Emulsions" Available at http://www2.chemie.uni-erlangen.de/services/dissonline/data/dissertation/Christoph_Wabel/html.
Lee et al., "The Application of NMR Techniques to the Structural Confirmation of O-Substituted 3,4-Dihydroxyphenylacetic Acid Derivatives", Bull. Korean Chem. Soc, vol. 13, No. 1, pp. 87-91 (1992) and Chemical Abstract XP-002305075 (2 pages).
Strazzolini et al, "Nitrolysis of t-Butyl and 1-Adamantyl Esters" Tetrahedron Letters, vol. 39, pp. 9255-9258 (1998).
Office Action dated Aug. 8, 2008 cited in copending U.S. Appl. No. 11/332,409.
Notice of Allowance dated Oct. 17, 2005 for U.S. Appl. No. 10/980,067.

(Continued)

*Primary Examiner*—Yvonne L Eyler
*Assistant Examiner*—Donna Jagoe
(74) *Attorney, Agent, or Firm*—Pepper Hamilton LLP

(57) ABSTRACT

The invention provides pharmaceutical compositions comprising a phenylacetic acid ester compound useful for inducing or maintaining general anesthesia or sedation in mammals, methods for preparing such compositions, and methods for inducing or maintaining anesthesia or sedation using such compositions.

3 Claims, No Drawings

OTHER PUBLICATIONS

Office Action dated Jun. 17, 2005 for U.S. Appl. No. 10/980,067.

Notice of Allowance dated Feb. 22, 2005 for U.S. Appl. No. 10/350,624.

Notice of Allowance dated Sep. 20, 2004 for U.S. Appl. No. 10/350,624.

Office Action dated May 28, 2004 for U.S. Appl. No. 10/350,624.

Clarke "The eugenols," Intravenous Anesthesia, Chapter 8, pp. 162-192 (1974).

MacKenzie et al., "Formulation and evaluation of a propanidid hydroxypropryl-beta-cyclodextrin solution for intravenous anesthesia," Int Journ of Pharmaceutics (1997) 159:191-196.

Swerdlow "A trial of propanidid (FBA.1420): a new ultrashort-acting anaesthetic," Brit J Anaesth (1965) 37 (10):785-789.

Wynands et al., "A clinical study of propanidid (FBA 1420)," Can Anaes Soc J (1985) 12(6):587-594.

Zipf et al., "[Local and endoanesthetic side effects of the short acting narcotic propanidide and some analogues. Effect of a solvent agent on the degree of effectiveness]," (1967) 17(8):1021-1028.

Notice of Allowance dated Nov. 25, 2008 received in counterpart U.S. Appl. No. 11/332,409.

HCAPLUS, Document No. 70:55895; Puetter, Johann (1968).

Office Action dated Apr. 14, 2010 in co pending U.S. Appl. No. 12/400,942.

* cited by examiner

PHARMACEUTICAL COMPOSITIONS OF SHORT-ACTING SEDATIVE HYPNOTIC AGENT

CROSS REFERENCE TO RELATED APPLICATIONS

This application claims the benefit of U.S. Provisional Application No. 60/489,559, filed Jul. 23, 2003, the entire disclosure of which is incorporated herein by reference.

FIELD OF THE INVENTION

The invention is directed to pharmaceutical compositions of a substituted phenylacetic acid ester compound which is useful as a short-acting sedative hypnotic agent for anesthesia and sedation. The pharmaceutical compositions are lipid emulsion formulations suitable for administration by injection.

BACKGROUND OF THE INVENTION

Sedative hypnotic agents are widely used for the induction and maintenance of general anesthesia, for sedation during surgical or diagnostic procedures and for sedation of patients in intensive care. Commonly assigned U.S. patent application Ser. No. 10/350,624 discloses the novel phenylacetic acid ester [4-[(N,N-diethylcarbamoyl)methoxy]-3-ethoxyphenyl]acetic acid propyl ester

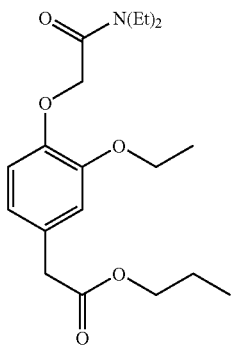

as a useful short-acting sedative hypnotic agent. Among other properties, [4-[(N,N-diethylcarbamoyl)methoxy]-3-ethoxyphenyl]acetic acid propyl ester is expected to be pharmacokinetically responsive, providing shorter and more predictable duration of action than other sedative hypnotic agents.

Agents for sedation and anesthesia are frequently administered by injection, a form of administration for which the agents need to be formulated in an aqueous medium. [4-[(N,N-Diethylcarbamoyl)methoxy]-3-ethoxyphenyl]acetic acid propyl ester, however, is an oleaginous compound, which is poorly, if at all soluble in aqueous media. The preparation of poorly soluble medicinal compounds for intravenous administration has been the subject of considerable investigation, but remains a significant challenge in the development of new therapeutic agents. For example, U.S. Pat. No. 4,711,902 discloses certain sparingly soluble medicinal compounds can be formulated as lipid emulsions using esters of medium chain length fatty acids as the lipid solvent. Propofol, 2,6-diisopropylphenol, is another oleaginous agent used for sedation and anesthesia. Propofol is currently provided commercially in the U.S. by AstraZeneca as Diprivan® Injectable Emulsion, at a 1% concentration in a soybean oil containing emulsion.

The lower the concentration of drug, the higher the ratio of lipid solvent to drug, and hence the higher the amount of lipids provided to the patient, with an attendant risk of hyperlipidemia, to produce the same therapeutic effect. It would be desirable to provide a formulation of [4-[(N,N-diethylcarbamoyl)methoxy]-3-ethoxyphenyl]acetic acid propyl ester suitable for injection at a sufficiently high drug concentration using ingredients appropriate for administration by injection. Furthermore, for use in practice, it would be desirable, for the formulation of [4-[(N,N-diethylcarbamoyl)methoxy]-3-ethoxyphenyl]acetic acid propyl ester to be sufficiently stable to permit storage.

SUMMARY OF THE INVENTION

The present invention provides pharmaceutical compositions of [4-[(N,N-diethylcarbamoyl)methoxy]-3-ethoxyphenyl]acetic acid propyl ester as lipid emulsions. The compositions comprise [4-[(N,N-diethylcarbamoyl)methoxy]-3-ethoxyphenyl]acetic acid propyl ester; a water-immiscible solvent; an emulsifier; a tonicity modifier; a pH buffering agent; and water; wherein the composition has a pH greater than about 7 and wherein the pH buffering agent is histidine which is present at a weight percentage of between about 0.05% and about 0.2%. In addition, the compositions comprise an optional stabilizing agent and an optional preservative. Further, the compositions are prepared by addition of a base, as needed, to adjust the pH.

The inclusion of histidine as a pH buffer as been demonstrated to increase the stability of the emulsions of the invention. Specifically inclusion of histidine has been shown to stabilize the pH, chemical composition, and particle size of the present emulsions.

In one embodiment, the water-immiscible solvent is soybean oil, the emulsifier is lecithin, and the tonicity modifier is glycerol. In this embodiment, oleic acid is present as the stabilizing agent, the preservative, if present, is ethylenediaminetetraacetic acid, and the pH is adjusted with NaOH. A specific composition comprises between about 2% and about 5%, by weight, [4-[(N,N-diethylcarbamoyl)methoxy]-3-ethoxyphenyl]acetic acid propyl ester, between about 15% and about 22%, by weight, soybean oil, between about 1.2% and about 2.6%, by weight, lecithin, between about 1.9% and about 2.8%, by weight, glycerol, between about 0.01% and about 0.1%, by weight, oleic acid, between about 0.05% and about 0.2%, by weight histidine, between about 0% and about 0.2%, by weight, and water, and optionally includes EDTA, the composition having a pH greater than about 7.

The invention also provides a method for inducing or maintaining anesthesia or sedation in a mammal comprising administering to the mammal a therapeutically effective amount of a pharmaceutical composition of the invention.

In another aspect, the invention provides a method of preparing a pharmaceutical composition, the method comprising combining an emulsifier, a stabilizing agent, a tonicity modifier, histidine in an amount sufficient to comprise between about 0.05% and about 0.2% by weight of the total composition, water, and optionally a preservative, to form an aqueous phase solution; adjusting the pH of the aqueous phase solution with base to a pH of greater than about 7; combining [4-[(N,N-diethylcarbamoyl)methoxy]-3-ethoxyphenyl]acetic acid propyl ester with a water-immiscible solvent to form a lipid phase mixture; adding the lipid phase mixture to the aqueous phase solution and emulsifying the resulting mixture to form the pharmaceutical composition. In a specific embodiment of the method, the water-immiscible solvent is soybean oil and the pH is adjusted to between about 7.9 and about 8.1.

DETAILED DESCRIPTION OF THE INVENTION

When describing the compositions and methods of the invention, the following terms have the following meanings, unless otherwise indicated.

The term "hypnotic agent" refers generally to a compound that promotes sleep. As used in pharmacology, the term "hypnotic agents" describe agents used to induce or maintain anesthesia, sedation, or sleep.

The term "anesthesia" as used herein means a loss of consciousness, sensation, or awareness resulting from pharmacological depression of nerve function.

The term "sedation" is defined herein as the calming of mental excitement or abatement of physiological function by administration of a drug.

The term "effective amount" means that amount which is sufficient to induce or maintain anesthesia or sedation when administered to a mammal. The effective amount will vary depending on the subject and the manner of administration, and may be determined routinely by one of ordinary skill in the art.

The term "analgesic" means a compound that relieves pain by altering perception of nociceptive stimuli without producing significant anesthesia or loss of consciousness.

The term "opioid" means a synthetic narcotic that has opiate-like activities (e.g., analgesia), but is not derived from opium.

The term "short-acting" as used herein refers to agents that are pharmacokinetically responsive. When short-acting agents are administered by infusion, the effects of the agents cease promptly upon termination of the infusion.

The term "isotonic" as used herein means having an osmotic pressure equal or similar to that of physiological fluids. Body fluids normally have an osmotic pressure that often is described as corresponding to that of a 0.9% (w/v) aqueous solution of sodium chloride.

The term "buffer" or "buffered" as used herein means a solution containing both a weak acid and its conjugate base, whose pH changes only slightly upon addition of acid or base. The term "buffering agent" means a species whose inclusion in a solution provides a buffered solution.

The present invention provides pharmaceutical compositions comprising the short-acting sedative hypnotic agent [4-[(N,N-diethylcarbamoyl)methoxy]-3-ethoxyphenyl]acetic acid propyl ester, hereinafter the "active agent", in a lipid emulsion formulation suitable for administration by injection.

The formulations are based on a water-immiscible solvent in which the active agent is miscible to a reasonable extent, such that a significant concentration of active agent can be achieved in the lipid emulsion. At the same time, it is desirable to minimize the ratio of solvent to active agent. In some embodiments, the ratio of solvent to active agent is less than about 7:1.

The water-immiscible solvent can be a plant-based oil, including but not limited to soybean oil, safflower oil, cottonseed oil, corn oil, sunflower oil, arachis (peanut) oil, castor oil, olive oil, sesame oil, coconut oil, almond oil, palm kernel oil, and mixtures thereof. Alternatively, the solvent is an ester of a medium-chain ($C_6$-$C_{12}$) or long-chain ($C_{14}$-$C_{24}$) fatty-acid, for example a mono-, di-, or triglyceride; an ester of a combination of a medium and long-chain fatty acid; or is a chemically modified or manufactured material such as a glycerol ester, polyoxyl, or a fractionated or hydrogenated plant-based oil. A fish oil, for example, cod liver oil or menhaden oil, is yet another alternative solvent.

In some embodiments, soybean oil is used as the water-immiscible solvent which forms the major component of the lipid phase. In these embodiments, soybean oil is present in the compositions at a weight percentage concentration of between about 15% and about 22%, including between about 18% and about 21%, and between about 18% and about 20%.

The pharmaceutical compositions also include an emulsifier, a tonicity modifier, a pH buffering agent, and water. Preferably, deionized water, suitable for injection, is used to prepare the compositions. The compositions can also optionally contain a stabilizing agent, a base to adjust pH, and a preservative, such as ethylenediaminetetraacetic acid (EDTA) or sodium metabisulphite.

Only a limited number of non-ionic emulsifiers, variously termed surfactants in the literature, is currently regarded as safe for parenteral administration. Principally, synthetic non-ionic emulsifiers such as ethoxylated ethers and esters, e.g. polyethyleneglycol sorbitan monooleate (Tween® 80), and phospholipids, of which lecithin is a particular example, are considered safe.

The term "lecithin" is used herein in its art-recognized manner. [See, for example, the United States Pharmacopeia/National Formulary, published by the United States Pharmacopeial Convention, Inc. (Rockville, Md.).] Lecithin includes a complex mixture of acetone-insoluble phosphatides, of which phosphatidylcholine is a significant component. The term lecithin is also used as a synonym for phosphatidylcholine. Commercially supplied lecithin is typically derived from egg yolk, soybeans, or corn.

In some embodiment of the present invention, lecithin is used as the emulsifier. In these embodiments, lecithin is present in the compositions at a weight percentage of between about 1.2% and about 2.6%, including between about 2.2% and about 2.5% and between about 2.2% and about 2.4%.

The pharmaceutical compositions can be made isotonic with blood by the incorporation of a suitable tonicity modifier. Suitable tonicity modifying agents include glycerol, xylitol, mannitol, and sorbitol. In some embodiments, glycerol is used as the tonicity modifying agent in a weight percentage concentration of between about 1.9% and about 2.8%, including between about 2.0% and about 2.6%, and between about 2.3% and about 2.5%.

The compositions are formulated to be at physiologically neutral pH, which is typically defined as the range 6.0-8.5. The compositions have a pH greater than about 7, including a pH in the range of between about 7.9 and about 8.1. The pH is adjusted by the addition of base, for example NaOH or $NaHCO_3$. Typically, less than 0.05% by weight of NaOH is added to adjust pH.

The compositions also include a pH buffering agent. Buffers used in products approved for intravenous administration include sodium phosphate, citric acid, sodium carbonate and bicarbonate, tris(hydroxy methyl) aminomethane (TRIS), diethanolamine, and amino acid buffers, such as histidine. A histidine buffer is preferred. Histidine contributes significant pH buffering capacity in the pH range of 6 to 8, having a $pK_a$ of about 6. Histidine is present in compositions according to the present invention at a weight percentage concentration of between about 0.05% and about 0.2%, including between about 0.09% and about 0.16%, and between about 0.09% and about 0.10%. A specific example of a useful histidine concentration is 0.10%. Another specific example of a useful histidine concentration is 0.15%.

The applicants have observed that absent a buffering agent, the pH of the composition can drop significantly upon processing of the emulsion and over time upon storage. As demonstrated in Example 7 below, inclusion of the histidine buffer is highly beneficial not only in controlling pH upon processing and reducing pH drift upon storage, but also in promoting stability in drug concentration on storage at low temperature and on exposure to elevated temperatures, such as those used in autoclaving in commercial manufacture of formulations. Further, compositions of the invention after having been exposed to elevated temperature demonstrated almost no change in particle size and less than about 4% change in drug concentration after storage at room temperature for 20 weeks.

The present compositions can also include a stabilizing agent, which can alternatively be considered as a co-emulsifier. Stabilizing agents are beneficial in promoting the physical stability of the emulsion over time, that is, in retarding separation of the oil and aqueous phases, on storage. Useful stabilizers include oleic acid and its sodium salt, cholic acid and deoxycholic acid and their respective salts, and cationic lipids such as stearylamine and oleylamine. Alternatively, anionic stabilizers, including phosphatidylethanolamines, conjugated with polyethylene glycol, (PEG-PE) and phosphatidylglycerols, a specific example of which is dimyristolphosphatidylgylcerol (DMPG), can be used. In some embodiments, oleic acid is used as the stabilizing agent. Oleic acid can be present at a weight percentage concentration of between about 0.01% and about 0.1%, including between about 0.02% and about 0.06%, and between about 0.03% and about 0.05%.

Finally, the compositions can include a preservative, typically ethylenediaminetetraacetic acid (EDTA), which can be provided as the disodium salt. For example, the compositions include between about 0% and about 0.2%, including between about 0% and about 0.015%, and between about 0% and about 0.0075% EDTA. In some embodiments, the composition does not include EDTA (0%). In other embodiments, the composition includes about 0.005% EDTA.

Using the components described above, stable emulsion formulations can be prepared that incorporate a significant concentration of [4-[(N,N-diethylcarbamoyl)methoxy]-3-ethoxyphenyl]acetic acid propyl ester, i.e. the active agent. In specific embodiments, the compositions include between about 2% and about 5%, including between about 3.6% and about 4.2%, and between about 3.7% and about 4% of the active agent by weight. In compositions in which soybean oil is used as the water-immiscible solvent, a specific ratio of soybean oil to active agent is between about 4:1 and about 6:1.

In one aspect, therefore, the present invention provides a pharmaceutical composition comprising [4-[(N,N-diethylcarbamoyl)methoxy]-3-ethoxyphenyl]acetic acid propyl ester; a water-immiscible solvent; an emulsifier; a tonicity modifier; histidine in a quantity sufficient to provide a weight percentage of between about 0.05% and about 0.2% histidine in the total composition, an optional stabilizing agent, an optional preservative, and water; wherein the composition has a pH greater than about 7.

In another aspect, the invention provides a pharmaceutical composition comprising [4-[(N,N-diethylcarbamoyl)methoxy]-3-ethoxyphenyl]acetic acid propyl ester, soybean oil, an emulsifier, a stabilizing agent, a tonicity modifier, a base, histidine in a quantity sufficient to provide a weight percentage of between about 0.05% and about 0.2% histidine in the total composition, and water, wherein the base is present in a quantity sufficient to provide the composition with a pH greater than about 7. In specific embodiments, the stabilizing agent is oleic acid at a weight percentage concentration of between about 0.01% and about 0.1%. Optionally, the above composition also includes a preservative.

The invention further provides a pharmaceutical composition comprising between about 2% and about 5%, by weight, [4-[(N,N-diethylcarbamoyl)methoxy]-3-ethoxyphenyl]acetic acid propyl ester, between about 15% and about 22%, by weight, soybean oil, between about 1.2% and about 2.6%, by weight, lecithin, between about 1.9% and about 2.8%, by weight, glycerol, between about 0.01% and about 0.1%, by weight, oleic acid, between about 0.05% and about 0.2%, by weight histidine, between about 0% and about 0.2%, by weight, EDTA, and water; wherein the composition has a pH greater than about 7.

Additionally, the invention provides a composition comprising between about 3.6% and about 4.2%, by weight, [4-[(N,N-diethylcarbamoyl)methoxy]-3-ethoxyphenyl]acetic acid propyl ester, between about 18% and about 21%, by weight, soybean oil, between about 2.2% and about 2.5%, by weight, lecithin, between about 2.0% and about 2.6%, by weight, glycerol, between about 0.02% and about 0.06%, by weight, oleic acid, between about 0.09% and about 0.16%, by weight histidine, between about 0% and about 0.015%, by weight, EDTA, and water; wherein the composition has a pH between about 7.9 and about 8.1.

In particular, the invention provides a composition comprising between about 3.7% and about 4%, by weight, [4-[(N,N-diethylcarbamoyl)methoxy]-3-ethoxyphenyl]acetic acid propyl ester, between about 18% and about 20%, by weight, soybean oil, between about 2.2% and about 2.4%, by weight, lecithin, between about 2.3% and about 2.5%, by weight, glycerol, between about 0.03% and about 0.05%, by weight, oleic acid, between about 0.09% and about 0.1%, by weight histidine, between about 0% and about 0.0075%, by weight, EDTA, and water; wherein the composition has a pH between about 7.9 and about 8.1.

The pharmaceutical compositions of the present invention can be used for the induction and/or maintenance of general anesthesia, for the initiation and/or maintenance of conscious sedation with patients spontaneously breathing, and for the induction and/or maintenance of sedation for intubated, mechanically ventilated patients. Thus, the invention also includes a method of inducing or maintaining anesthesia or sedation in a mammal, the method comprising administering to the mammal an effective amount of a pharmaceutical composition of the invention.

The amount of the active agent required for use in the methods of the invention will vary with the route of administration, the age and condition of the patient, and the degree of anesthesia or sedation required, and will be ultimately at the discretion of the attendant physician or clinician.

In general, the compositions can be administered as an initial bolus dose to produce anesthesia or sedation, followed by a continuous infusion of composition at a rate that is sufficient to achieve and maintain the level of anesthesia or sedation desired. Alternatively, a continuous infusion of a composition of the present invention can be used to maintain anesthesia or sedation following induction or induction and maintenance with another sedative hypnotic agent, (e.g. propofol, a barbiturate, such as nembutal® (pentobarbital sodium) or brevital® sodium (methohexital sodium), or a benzodiazepine, such as valium®).

For example, a suitable bolus dose of the present agent for a human patient will typically be in the range of from about 0.1 to about 50 milligrams/kilogram (mg/kg), preferably about 0.5 to about 20 mg/kg. The rate of infusion will typically be in the range from about 5 to about 5000 micrograms/kilogram/minute (µg/kg/min), preferably about 10 to about 2000 µg/kg/min.

The compositions of the invention can also be administered in combination with other therapeutic agents, such as, for example, other sedative hypnotic agents, analgesics (e.g. an opioid such as the µ-opioid agonist remifentanil, fentanyl, sulfentanil, or alfentanil), or paralytic agents, such as atracurium besylate or pancuronium bromide. Accordingly, the compositions of the invention can optionally further comprise another therapeutic agent, for example, a sedative hypnotic agent, analgesic, or paralytic agent. Similarly, the therapeutic methods of the invention can also optionally comprise administering another therapeutic agent (e.g. a sedative hypnotic agent, analgesic, or paralytic agent) to the mammal.

The pharmaceutical compositions are prepared by combining the water phase components, i.e. the emulsifier, tonicity modifier, a quantity of histidine sufficient to comprise between about 0.05% and about 0.2% by weight of the total composition, optional stabilizing agent, optional preservative, and water at elevated temperature and adjusting the pH with base, as required, to a value greater than about 7 while the solution is still warm. The active agent is combined with the water-immiscible solvent, heated until miscible and then added to the water phase mixture. The resultant mixture is emulsified to form the pharmaceutical composition.

In one example, as described in greater detail below, a pharmaceutical composition is prepared by combining the water phase components, i.e. the emulsifier, stabilizing agent, tonicity modifier, histidine, preservative, if present, and water at elevated temperature and adjusting the pH to between about 7.9 and about 8.1 with base while the solution is still warm. The active agent is combined with soybean oil, heated until miscible and then added to the water phase mixture. The solution is stirred to form a pre-mixed solution, which is subsequently emulsified using a microfluidizer operated at a pressure of about 12000 to about 15000 psi for about 30 seconds. Accordingly, the invention further provides methods of preparing a pharmaceutical composition.

As described above and in the appended examples, one of the principal benefits of including histidine in the lipid emulsion compositions of the invention is stabilizing the pH of the composition upon emulsification and upon storage. Accordingly, the invention further provides a method of stabilizing the pH of an emulsion having a pH greater than about 7, the emulsion comprising [4-[(N,N-diethylcarbamoyl)methoxy]-3-ethoxyphenyl]acetic acid propyl ester, a water-immiscible solvent, and water, the method comprising including a weight percentage of histidine of between about 0.05% and about 0.2% in the emulsion.

The active agent, [4-[(N,N-diethylcarbamoyl)methoxy]-3-ethoxyphenyl]acetic acid propyl ester, compound 1, can be synthesized from readily available starting materials as shown in the following Scheme and further described in the Examples below. It will be appreciated that while specific process conditions (i.e. reaction temperatures, times, mole ratios of reactants, solvents, pressures etc.) are given, other process conditions can also be used unless otherwise stated.

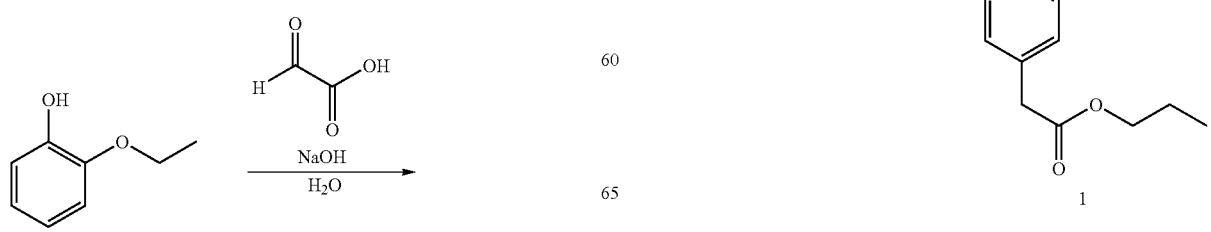

Intermediate 2, (3-ethoxy-4-hydroxyphenyl)hydroxy-acetic acid can be prepared by addition of base to an aqueous mixture of 2-ethoxyphenol and glyoxylic acid cooled to 0° C. Intermediate 3, acetoxy-(4-acetoxy-3-ethoxyphenyl)-acetic acid, can be formed by the addition of acetic anhydride to intermediate 2 dissolved in dichloromethane (DCM) and pyridine, cooled in an ice bath. Intermediate 3 dissolved in a short chain alcohol is reduced under hydrogen to provide intermediate 4, (4-acetoxy-3-ethoxyphenyl)-acetic acid, which is reacted with an excess of propanol and a catalytic amount of concentrated $H_2SO_4$ to form the propyl ester, intermediate 5, (3-ethoxy-4-hydroxyphenyl)-acetic acid propyl ester. Finally, intermediate 5 is reacted with a compound of the structure X—$CH_2C$(=O)N(Et)$_2$, where X is a leaving group, in the presence of potassium carbonate to provide the active agent, compound 1.

The following non-limiting examples illustrate preparation of the active agent, [4-[(N,N-diethylcarbamoyl)methoxy]-3-ethoxyphenyl]acetic acid propyl ester, compound 1, and preparation of representative pharmaceutical compositions of the invention.

In the examples below, the following abbreviations have the following meanings. Any abbreviations not defined have their generally accepted meaning. Unless otherwise stated, all temperatures are in degrees Celsius.

| | |
|---|---|
| DMSO = | dimethylsulfoxide |
| EtOAc = | ethyl acetate |
| DCM = | dichloromethane |
| PPTS = | pyridinium para-toluene sulphonate |
| DMF = | dimethylformamide |

General: Unless noted otherwise, reagents, starting material and solvents were purchased from commercial suppliers, for example Sigma-Aldrich (St. Louis, Mo.) and Trans World Chemicals, Inc. (TCI) (Rockville, Md.), and used without further purification; reactions were run under nitrogen atmosphere; reaction mixtures were monitored by thin layer chromatography (silica TLC), analytical high performance liquid chromatography (anal. HPLC), or mass spectrometry; reaction mixtures were commonly purified by flash column chromatography on silica gel, or by vacuum distillation; NMR samples were dissolved in deuterated solvent ($CD_3OD$, $CDCl_3$, or DMSO-d6), and spectra were acquired with a Varian Gemini 2000 instrument (300 MHz) using the listed solvent as the internal standard unless otherwise indicated; and mass spectrometric identification was performed by an electrospray ionization method (ESMS) with a Perkin Elmer instrument (PE SCIEX API 150 EX).

EXAMPLE 1

Synthesis of
(3-ethoxy-4-hydroxyphenyl)hydroxy-acetic acid (2)

2-Ethoxyphenol (56.6, 0.401 mol, 1 eq.), glyoxylic acid (50% aqueous solution) (41.0 mL, 0.396 mol, 0.99 eq.), and distilled water (110 mL) were combined. The mixture was cooled in an ice bath, and a solution of 10% NaOH (32.2 g NaOH in 300 mL distilled water, 0.805 mol, 2 eq.) was slowly added via addition funnel. The reaction was allowed to slowly warm to room temperature, and after ~18 hours, the solution was washed with ethyl acetate (4×250 mL), then acidified with 6N HCl until pH ~3. NaCl was added and the product was then extracted into ethyl acetate (4×200 mL). The organic phase was washed with brine, dried over magnesium sulfate, and solvent was removed under vacuum, giving 51.8 g of intermediate 2 as a light pink solid.

$^1$H NMR (DMSO-$d_6$, 300 MHz): δ 1.24 (t, 3H), 3.90 (q, 2H), 4.79 (s, 1H), 5.59 (bs, 1H), 6.67 (q, 2H), 6.86 (s, 1H), 8.81 (s, 1H), 12.35 (bs, 1H).

EXAMPLE 2

Synthesis of
acetoxy-(4-acetoxy-3-ethoxyphenyl)-acetic acid (3)

Intermediate 2 (45.0 g, 0.212 mol, 1 eq.) was dissolved in DCM (225 mL), pyridine (80 mL, 0.989 mol, 6 eq.) was added and the mixture was cooled in an ice bath under nitrogen. Acetic anhydride (100 mL, 1.06 mol, 4 eq.) was added slowly via addition funnel. The mixture was stirred (~3 hr) until reaction was complete and then diluted with diethyl ether (500 mL) and washed with 1N HCl (4×250 mL). The mixture was extracted into 8% sodium bicarbonate solution (4×80 mL), acidified to ~pH 4 with 6N HCl, and the product extracted into diethyl ether, giving 41.1 g of intermediate 3 as a white crystalline solid.

$^1$H NMR (DMSO-$d_6$, 300 MHz): δ 1.12 (t, 3H), 2.05 (s, 3H), 2.17 (s, 3H), 3.95 (q, 2H), 5.72 (s, 1H), 6.96 (d, 1H), 7.04 (d, 1H), 7.12 (s, 1H).

EXAMPLE 3

Synthesis of (4-acetoxy-3-ethoxyphenyl)-acetic acid (4)

Intermediate 3 (30.9 g, 0.104 mol) was dissolved in methanol (500 mL), Pd(OH)$_2$ (5.0 g) wet with distilled water was added, and the mixture was placed under hydrogen at 30 psi with shaking. After 48 hr Pd(OH)$_2$ was removed by filtration and solvent was removed under vacuum giving 22 g of intermediate 4 as a yellow oil.

$^1$H NMR (DMSO-$d_6$, 300 MHz): δ 1.19 (t, 3H), 2.16 (s, 3H), 3.47 (s, 2H), 3.92 (q, 2H), 6.74 (d, 1H), 6.91 (m, 2H).

EXAMPLE 4

Synthesis of (3-ethoxy-4-hydroxyphenyl)-acetic acid propyl ester (5)

Intermediate 4 (1.40 g, 5.87 mmol) was dissolved in an excess of 1-propanol (50 mL), concentrated H$_2$SO$_4$ (3 drops) was added, and the mixture was heated at 90° C. for ~18 hours. The volume of 1-propanol was reduced under vacuum, then the mixture was diluted with diethyl ether, washed with saturated sodium bicarbonate solution (2×), distilled water (1×), brine (1×), dried over magnesium sulfate and solvent was removed under vacuum, giving intermediate 5 as a yellow oil.

$^1$H NMR (DMSO-$d_6$, 300 MHz): δ 0.78 (t, 3H), 1.25 (t, 3H), 1.48 (q, 2H), 3.44 (s, 2H), 3.92 (m, 4H), 6.58 (d, 1H), 6.64 (d, 1H), 6.74 (s, 1H), 8.73 (s, 1H).

EXAMPLE 5

Synthesis of [4-[(N,N-Diethylcarbamoyl)methoxy]-3-ethoxyphenyl]acetic acid propyl ester (1)

In a 50 mL round bottom flask equipped with a magnetic stir bar, 3-ethoxy-4-hydroxyphenylacetic acid propyl ester (5) (800 mg, 3.4 mmol, 1.0 equiv.) was dissolved in dry acetone (20 mL). To the solution was added $K_2CO_3$ (705 mg, 5.1 mmol, 1.5 equiv.) followed by 2-chloro-N,N-diethylacetamide (0.55 mL, 4.0 mmol, 1.2 equiv., available from Aldrich). Under vigorous stirring, the suspension was warmed to reflux and kept under those conditions for 15 hours. After cooling to room temperature the reaction mixture was filtered through a folded paper filter and the remaining solution freed of solvent under reduced pressure. The oily product was purified by column chromatography ($SiO_2$, 50% EtOAc/hexane) to yield 630 mg (53% of theory) of colorless oil which was 99.6% pure by HPLC.

TLC (silica, 50% EtOAc/hexane) $R_f$ 0.25; $^1H$ NMR ($CDCl_3$, 300 MHz) d 0.90 (3H, t, propylate $CH_3$), 1.13 and 1.20 (each 3H, t, N-ethyl $CH_3$), 1.43 (3H, t, ethoxy $CH_3$), 1.60-1.67 (2H, m, propylate $CH_2$), 3.35-3.46 (4H, m, N-ethyl $CH_2$), 3.53 (2H, s, $OCH_2CO$), 4.01-4.11 (4H, m, 2×$OCH_2$), 4.70 (2H, s, $ArCH_2CO$), 6.75-6.91 (3H, m, ArH). m/z: [M+H$^+$] calcd for $C_{19}H_{29}NO_5$ 352.22; found 352.

EXAMPLE 6

Preparation of Pharmaceutical Compositions of Compound 1

Pharmaceutical compositions were prepared according to the following procedure. A mixture of L-α-phosphatidylcholine 60% (lecithin) (product P-5394, Sigma-Aldrich, St. Louis, Mo.), glycerol (98%) (Sigma-Aldrich), oleic acid (99%) (Fluka-Sigma-Aldrich, Buchs, Switzerland), histidine (Fresenius Kabi, Clayton, N.C.), EDTA disodium salt (Sigma-Aldrich), if present, and deionized water was heated at 60° C. until fully dissolved giving a semi-opaque solution. The pH was adjusted to pH 8.0 while the solution was still warm by addition of 0.1 N NaOH. A mixture of compound 1 and soybean oil (Sigma-Aldrich) was heated to 60° C. until miscible and then added to the first mixture. The solution was stirred briefly at 60° C. and then transferred to a beaker and stirred with a Polytron tissue homogenizer for 5 min at maximum speed to provide a premixed solution.

A microfluidizer (Microfluidics Corp., Newton, Mass., model no. 110S) was washed with isopropanol and then deionized water. The microfluidizer was primed with a minimal amount of the premixed solution. The reservoir of the microfluidizer was filled with the premixed solution and the solution was circulated through the mixing chamber for 30 sec at maximum pressure (~12000-15000 psi). The first ~10 drops of microfluidized solution were collected and discarded, then all subsequent fractions were collected in a glass vial.

The weight of reagents used to prepare Samples A through F is given in Table 1A. In these preparations, titration required between about 0.5 and about 1.5 mL of 0.1 N NaOH depending on the histidine content.

TABLE 1A

| | Quantity of Reagents (g) | | | | | |
|---|---|---|---|---|---|---|
| Reagent | Sample A | Sample B | Sample C | Sample D | Sample E | Sample F |
| compound 1 | 2.006 | 1.995 | 2.005 | 1.998 | 1.999 | 2.000 |
| soybean oil | 10.020 | 10.030 | 10.020 | 10.040 | 10.050 | 10.030 |
| lecithin | 1.199 | 1.203 | 1.200 | 1.200 | 1.203 | 1.203 |
| glycerol | 1.252 | 1.254 | 1.251 | 1.251 | 1.249 | 1.253 |
| oleic acid | 0.027 | 0.027 | 0.027 | 0.027 | 0.027 | 0.018 |
| water | 35.800 | 36.600 | 35.700 | 35.800 | 36.100 | 38.790 |
| histidine | 0.000 | 0.025 | 0.050 | 0.075 | 0.101 | 0.050 |
| % histidine | 0.00% | 0.05% | 0.10% | 0.14% | 0.19% | 0.09% |

The weight of reagents used to prepare Samples G and H, and the resulting weight percentage compositions are given in Table 1B. Titration required about 1 mL of 0.25 N NaOH. A 0.1 M solution of the disodium salt of EDTA was used in the preparation of the composition of Sample H.

TABLE 1B

| | Quantity of Reagents (g) and Percentage Composition | | | |
|---|---|---|---|---|
| | Weight (g) | | Weight Percentage | |
| Reagent | Sample G | Sample H | Sample G | Sample H |
| compound 1 | 6.000 | 6.013 | 4.04% | 4.04% |
| soybean oil | 30.030 | 30.000 | 20.20% | 20.16% |
| lecithin | 3.601 | 3.604 | 2.42% | 2.42% |
| glycerol | 3.752 | 3.754 | 2.52% | 2.52% |
| oleic acid | 0.059 | 0.058 | 0.04% | 0.04% |
| water | 104.100 | 104.000 | 70.01% | 69.89% |
| histidine | 0.150 | 0.150 | 0.10% | 0.10% |
| EDTA · 2Na (0.1 M) | — | 0.235 | 0% | 0.005% |

EXAMPLE 7

Characterization of Pharmaceutical Compositions of Example 6

Samples of the compositions were stored in sealed vials at room temperature (25° C.) and at 4° C. Periodically a sample was removed and analyzed. Stability of the compositions under exposure to high temperature and pressure, such as conditions encountered during autoclaving, was probed by sealing about 5 mL of sample in a 50 mL pressure tube and placing the tubes in an oil bath at greater than 120° C. for at least 15 min. The tubes were cooled in an ice bath and samples removed for analysis.

The pH of the compositions before emulsification in the microfluidizer (denoted premix), initially after formulation, after 2 weeks of storage at room temperature, after 20 weeks of storage at room temperature, after 2 weeks of storage at 4° C., and upon exposure to high temperature are listed in Table 2. The last column reports the pH of samples stored for 20 weeks at room temperature after having been exposed to the high temperature conditions. Samples were allowed to return to room temperature before measuring pH with an Orion model 520A probe pH meter.

TABLE 2 pH of Pharmaceutical Compositions

| Sample | Premix | Initial | 2 wks 25° C. | 20 wks 25° C. | 2 wks 4° C. | High Temp | High Temp stored for 20 wks 25° C. |
|---|---|---|---|---|---|---|---|
| A | 8.0 | 6.4 | 5.5 | 3.8 | 5.9 | 5.7 | 3.6 |
| B | 8.0 | 7.3 | 6.7 | 6.1 | 6.9 | 7.3 | 6.0 |
| C | 8.0 | 7.6 | 6.8 | 6.5 | 6.9 | 7.4 | 6.3 |
| D | 8.0 | 8.2 | 7.2 | 6.8 | 7.6 | 8.0 | 6.5 |
| E | 8.0 | 8.2 | 7.5 | 6.7 | 7.4 | 8.1 | 6.6 |

Initial concentrations of compound 1 in mg/mL and change in concentration after storage for 2 weeks at 25° C. and at 4° C., and after exposure to high temperatures are listed in Table 3. The last column reports the drug concentration of samples stored for 20 weeks at room temperature after having been exposed to the high temperature conditions. After 20 weeks of storage at room temperature, the emulsions of compositions having 0% and 0.05% histidine (Samples A and B) that had been exposed to high temperature conditions had started to separate.

Concentrations were determined by HPLC analysis using an Agilent 1100 Series instrument with a Zorbax RP-bonus 150×4.6 mm, 5 μm column. The mobile phases used were A: 0.1% TFA in 98:2 water:acetonitrile and B: 0.1% TFA in 10:90 water:acetonitrile. Detection was by UV absorbance at 289 nm. A flow rate of 2 mL/min and an initial condition 2% B for 0.3 min was used. The gradient was 2% to 80% B in 2.7 min, 80% to 100% B in 1.45 min and 100% to 2% B in 0.2 min.

TABLE 3

Concentration of Compound 1 (mg/mL) of Pharmaceutical Compositions

| Sample | Initial | Change 2 wks 25° C. | Change 2 wks 4° C. | Change High Temp | Conc High Temp | High Temp stored for 20 wks 25° C. |
|---|---|---|---|---|---|---|
| A | 44.0 | −3.1 | −8.5 | −7.2 | 36.8 | |
| B | 41.6 | 0.1 | −4.8 | −1.0 | 40.6 | |
| C | 43.3 | −5.4 | −4.9 | −2.0 | 41.3 | 40.2 |
| D | 42.5 | −0.6 | −5.0 | −1.9 | 40.6 | 40.0 |
| E | 41.7 | −1.1 | −4.3 | −2.2 | 39.5 | 38.0 |
| G | | | | | 42.3 | |
| H | | | | | 43.1 | |

Mean particle size of compositions after storage for 2 weeks at 25° C. and at 4° C., after exposure to high temperatures, and after storage for 20 weeks following exposure to high temperature are listed in Table 4. Numbers in parentheses, where given, are standard deviations of the particle size distributions. Particle size analysis was conducted using a Coulter N4 plus mode analyzer operated at a temperature of 20° C. and at an angle of 90 degrees. Samples were diluted in water to achieve intensity of about $2 \times 10^5$.

TABLE 4

Mean Particle Size (nm) of Pharmaceutical Compositions

| Sample | 2 wks 25° C. | 2 wks 4° C. | High Temperature | High Temp stored for 20 wks 25° C. |
|---|---|---|---|---|
| A | 213 | 205 | 490 | |
| B | 184 | 184 | 234 | |
| C | 183 | 184 | 238 | 241 (46) |
| D | 204 | 177 | 205 | 210 (45) |
| E | 177 | 178 | 233 | 237 (48) |
| G | | | 302 (60) | |
| H | | | 317 (61) | |

Inclusion of a histidine buffer in Samples B through E resulted in reduction of changes in pH upon emulsification, storage, and exposure to high temperature, as compared with Sample A, which does not contain a histidine component. The stabilization of pH over that of Sample A is particularly marked after storage for 20 weeks. Samples including a histidine buffer also demonstrate improved stability in concentration on exposure to high temperature and on storage at 4° C. as compared with Sample A. Compositions of the invention, specifically those of Samples C, D, and E, that had been exposed to high temperature conditions demonstrated less than 4% change in concentration and negligible change in particle size after storage for 20 weeks at room temperature. In addition, Samples B through E and G and H all had a mean particle size less than about 330 nm even after exposure to high temperature.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method of preparing a pharmaceutical composition, the method comprising the steps of:
    combining an emulsifier, a tonicity modifier, histidine in a quantity sufficient to comprise between about 0.05% and about 0.2% by weight of the composition, water, and optionally a stabilizing agent and a preservative to form an aqueous phase solution
    adjusting the pH of the aqueous phase solution with base, as required, to a pH of greater than about 7;
    combining [4-[(N,N-diethylcarbamoyl)methoxy]-3-ethoxyphenyl]acetic acid propyl ester with a water-immiscible solvent to form a lipid phase mixture; and
    adding the lipid phase mixture to the aqueous phase solution and emulsifying the resulting mixture to form the pharmaceutical composition.

2. The method of claim 1 comprising adjusting the pH of the aqueous phase solution with base to a pH of between about 7.9 and about 8.1; and wherein the water-immiscible solvent is soybean oil.

3. A method of stabilizing the pH of an emulsion having a pH greater than about 7, the emulsion comprising [4-[(N,N-diethylcarbamoyl)methoxy]-3-ethoxyphenyl]acetic acid propyl ester, a water-immiscible solvent, and water, the method comprising including a weight percentage of histidine of between about 0.05% and about 0.2% in the emulsion.

* * * * *